United States Patent [19]

Plattner et al.

[11] 4,166,825
[45] Sep. 4, 1979

[54] CHROMOGENIC SUBSTRATES

[75] Inventors: Jacob J. Plattner; Houston F. Voss, both of Libertyville; Susan E. Magic, Lake Bluff, all of Ill.

[73] Assignee: Abbott Laboratories, North Chicago, Ill.

[21] Appl. No.: 934,298

[22] Filed: Aug. 17, 1978

[51] Int. Cl.² .......................................... C07C 153/09
[52] U.S. Cl. .................................. 260/455 R; 560/34
[58] Field of Search ....................... 260/455 R; 560/34

[56] References Cited

U.S. PATENT DOCUMENTS

| | | | |
|---|---|---|---|
| 3,884,896 | 5/1975 | Blomback et al. | 260/112.5 R |
| 3,886,136 | 5/1975 | Claeson et al. | 260/112.5 R |
| 3,966,701 | 6/1976 | Dorman et al. | 260/112.5 R |

OTHER PUBLICATIONS

Klausner, et al., Interaction of α-N-(p-Toluenesulphonyl)-p-guanidino-L-phenylalanine. . ., Biochem. J., (1978), 169, pp. 157-167.

Farmer, et al., Use of N-benzoyl-L-tyrosine Thiobenzyl Ester as a Protease Substrate, Journal of Biological Chemistry, vol. 250, No. 18, pp. 7366-7371, (1975).

*Primary Examiner*—Alan L. Rotman
*Assistant Examiner*—Robert C. Whittenbaugh
*Attorney, Agent, or Firm*—John J. McDonnell; Robert L. Niblack

[57] ABSTRACT

The present invention encompasses acid addition salts of a compound of the formula

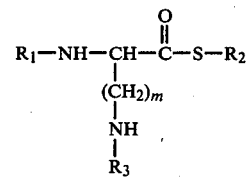

wherein: $R_1$ represents phenylsulfonyl, benzoyl, carbobenzoxy, and the halo, loweralkyl having 1-4 carbon atoms, loweralkoxy having 1-3 carbon atoms, phenyl, or hydroxy substituted derivatives thereof; or alkanoyl having 2-12 carbon atoms; $R_2$ represents alkyl having 1-10 carbon atoms, alkoxyalkyl having 2-6 carbon atoms, cycloalkyl having 5-7 carbon atoms, benzyl and the halo, loweralkyl having 1-4 carbon atoms, loweralkoxy having 1-3 carbon atoms, carboxy, hydroxy, or substituted derivatives thereof; $R_3$ represents hydrogen or guanyl, and m is 3 or 4.

Compounds of the present invention are useful as analytical reagents. Enzymatic hydrolysis provides —S—$R_2$ which can be further reacted with 5,5'-dithiobis (2-nitrobenzoic acid) to provide a colored product by which the enzyme concentration can be determined spectrophotometrically.

9 Claims, No Drawings

CHROMOGENIC SUBSTRATES

BACKGROUND OF THE INVENTION

The present invention relates to synthetic reagents or substrates which are used for the quantitative determination of proteolytic enzymes. More particularly, the invention relates to synthetic thioesters which are useful as a reagent for the quantitative determination of proteolytic enzyme of class E.C. 3.4.31, which split peptide chains on the carboxyl side of arginine as well as lysine in human and mammal body fluids as well as in vegetable and animal cell extracts and in glandular venoms of cold-blooded animals such as snakes.

Classical substrates for trypsin, thrombin and related enzymes have involved both esters such as α-N-tosyl-L-arginine methyl ester and α-N-tosyl-L-lysine methyl ester [G. W. Schwert et al., J. Biol. Chem. 172 (1948) 221; Sherry, S. and Troll, W., J. Biol. Chem. 208 (1954) 95; Elmore, D. T. and Curragh, Z. F. *Biochem. J.*, 86 (1963) 98] as well as amides such as α-N-benzoyl-DL-arginine-p-nitroanilide, L-lysine-p-nitroanilide, α-N-benzoyl-DL-arginine-2-naphthylamide and other di, tri and higher order arginine and lysine peptides with chromogenic amide leaving groups [B. F. Erlenger et al., *Arch. Bioch. Biop.* 96 (1961) 271; A. Reidel and E. Wunsch, *Z. Physiol. Chem.* 316 (1959) 1959; R. E. Plapinger et al., *J. Org. Chem.* 30 (1965) 1781; L. Svendsen et al., *Thrombosis Res.* 1 (1972) 267].

The use of ester substrates for this class of enzyme have been limited by the cumbersome assay procedures such as pH titration or detection of the small change in absorbance of the above products in the UV region of the spectra. The introduction of the amide chromogenic substrates based on p-nitroaniline or similar leaving groups have offered the advantage of an assay in the visible region of the spectra with by-products which have high extraction coefficients enabling more sensitive enzyme determinations to be made. The simple chromogenic substrates based only upon arginine or lysine amides have proved to be extremely poor substrates relative to the analogous esters [Erlinger et al., *Arch. Bioch. Biop.* 95 (1961) 271-8]. The advantage of extending the amino terminal end of either arginine or lysine p-nitroanilide substrates has been well documented and results in much improved substrate behavior, especially as determined by typical Michaelis-Menten kinetic parameters [Thrombosis Res 1 (1972) 267-78; U.S. Pat. No. 3,884,896, U.S. Pat. No. 4,061,625]. The difficulty in synthesizing these tri and tetra peptide materials has resulted in a high cost of the substrates and at the same time certain disadvantages such as limited stability and inhibition of the enzymes by the cleaved product, p-nitroaniline.

Farmer and Hageman, the Journal of Biological Chemistry, 250, 7366 (1975) describe the use of N-benzyoyl-L-tyrosine thiobenzyl ester as a protease substrate detected by further reaction with 5,5'-dithiobis (2-nitrobenzoic acid).

BRIEF DESCRIPTION OF THE INVENTION

The present invention encompasses acid addition salts of a compound of the formula

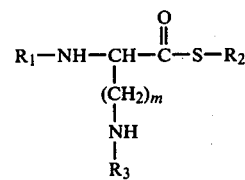

wherein $R_1$ represents phenylsulfonyl, benzoyl, carbobenzoxy, and the halo, loweralkyl having 1-4 carbon atoms, loweralkoxy having 1-3 carbon atoms, phenyl, or hydroxy substituted derivatives thereof; or alkanoyl having 2-12 carbon atoms; $R_2$ represents alkyl having 1-10 carbon atoms, alkoxyalkyl having 2-6 carbon atoms, cycloalkyl having 5-7 carbon atoms, or benzyl and the halo, loweralkyl having 1-4 carbon atoms, loweralkoxy having 1-3 carbon atoms, hydroxy, or phenyl substituted derivatives thereof; $R_3$ represents hydrogen or guanyl; and m is 3 or 4.

Compounds of the present invention are useful as analytical reagents for detecting enzymes such as thrombin and trypsin. Enzymatic hydrolysis provides —S—$R_2$ which can be further reacted with 5,5'dithiobis (2-nitrobenzoic acid) to produce a colored product by which the enzyme concentration can be indirectly determined spectrophotometrically.

DETAILED DESCRIPTION OF THE INVENTION

The present invention encompasses lysine and arginine derivatives

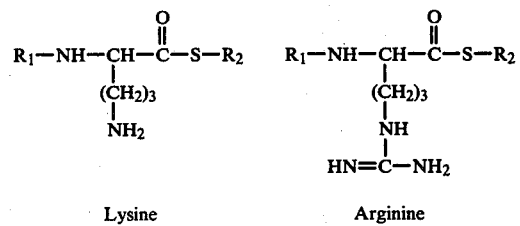

Lysine                Arginine $R_1$ previously defined, represents common blocking groups for the amino moiety of an amino acid. Thus, $R_1$ is typically a radical of the formula

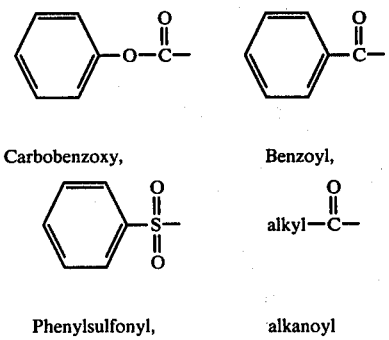

Carbobenzoxy,        Benzoyl,

Phenylsulfonyl,      alkanoyl

The phenyl ring may be substituted with common substituents including: halo such as fluoro, chloro, bromo, and iodo; loweralkyl such as methyl, isopropyl, propyl, butyl, isobutyl, tertiary butyl, alkoxy such as methoxy, ethoxy, propoxy, hydroxy and phenyl. Those skilled in the chemical arts will recognize the equivalence of a large number of aromatic ring substituents.

The above indicated blocking groups are introduced into lysine, arginine, homoarginine or homolysine by reacting methyl or ethyl ester of arginine, homoarginine, lysine or homolysine having the guanyl or ε-amino group, respectively blocked by protonization with acids such as nitric or p-toluene sulfonic with an activated ester of the blocking group such as p-nitrophenylester, pentachlorophenylester, N-hydroxysuccinimideester, acid azide, acid chloride, or acid anhydride. These techniques are well recognized in the peptide synthesis art, *J. Chem. Soc.*, 3134 (1957). Many blocked lysine and arginine acids and esters useful for preparing compounds of the present invention are known or commercially available [Archives of Biochemistry and Biophysics, 108, 266 (1964) and U.S. Pat. No. 3,884,896]. These blocked acids and esters are converted to compounds of the present invention by exchanging esters with thiols corresponding to $H-S-R_2$ in acid or by converting blocked amino acids to the acid chloride by reaction with thionyl chloride followed by reaction with the $H-S-R_2$ thiol, or by carbodiimide coupling of the mercaptan and the blocked amino acid.

Typically, $R_2$ is straight or branched chain loweralkyl having 1-10 carbon atoms exemplified by methyl ethyl, propyl isopropyl, butyl, isobutyl, pentyl, hexyl, decyl and the like, cyclopentyl, cyclohexyl, cycloheptyl, ethoxyethyl, metoxypropyl are examples of other groups represented by $R_2$. $R_2$ also represents benzyl and benzyl substituted with halo such as fluoro, chloro, bromo, iodo, loweralkyl such as methyl, ethyl, propyl, isopropyl, butyl, isobutyl, tertiary butyl; alkoxy such as methoxy, ethoxy; hydroxy; carboxy; and phenyl. Phenyl substituted benzyl is meant to include biphenylmethyl and naphthylmethyl.

In a typical preparation α-N-p-toluenesulfonyl-L-arginine is reacted with an excess of thionyl chloride to provide the corresponding acid chloride. The acid chloride is in turn reacted with ethyl mercaptan to provide α-N-(p-toluenesulfonyl)-L-arginine thioethylester hydrochloride which is purified by silica gel chromatography. Other acid addition salts are prepared by exchanging the anion on an ion exchange column, in this way acid salts such as sulfuric, hydrobromic, toluene sulfonic, sulfonic, phosphoric, acetic, carbonic, formic, benzoic, nitric, hydriodic, tetrafluoro boric acid and the like are prepared. The acid salts are of the type which are biologically compatible or pharmaceutically acceptable salts.

Preferred reagents in the scope of the present invention are the acid addition salts of α-N-(p-toluenesulfonyl)-L-arginine thioethylester
α-N-(p-toluenesulfonyl)-L-arginine thiobenzylester
α-N-(p-toluenesulfonyl)-L-arginine thioisopropylester
α-N-(p-toulenesulfonyl)-L-arginine thioisobutylester
α-N-(p-toulenesulfonyl)-L-arginine thio-p-chlorobenzylester
α-N-(p-toulenesulfonyl)-L-arginine thio-p-carboxybenzylester
P-N-(p-phenylsulfonyl)-L-arginine thiodecylester
α-N-(p-methoxyphenylsulfonyl)-L-arginine thiocyclohexylester
α-N-benzoyl-L-arginine thiobenzylester
α-N-carbobenzoxy-L-arginine tioethylester
α-N-carbobenzoxy-L-arginine thiobenzylester
α-N-benzoyl-L-arginine thioethylester
α-N-acetyl-L-lysine-thio-p-fluorobenzylthioester
α-N-pivalyl-L-lysine-thio-p-ethoxybenzylthioester
P-N-p-chlorobenzoyl-L-lysine-thio-p-toluenethioester
α-N-p-bromobenzoyl-L-lysine-thio-methylnapthylthioester.

Preferably the hydrochloride salts thereof.

Table 1 illustrates the usefulness of compounds of the present invention for determining thrombin and trypsin. Kinetic analysis of the compounds in Table 1 were carried out in pH 7.4, 0.1 M potassium phosphate buffer with 0.1% gelatin to stabilize the enzymes used. Both purified trypsin and purified thrombin were utilized to obtain the indicated Michaelis-Menten kinetic constants. The analyses were performed with 0.16 mM of 5,5' dithiobis-(2-nitrobenzoic acid) in the reaction mixture and varying concentrations of enzymes as warranted by the turnover of the indicated substrate. The analyses were formed in a routine manner on an Abbott ABA-100 bichromatic analyzer with a 415-550 filter pair at 37° C. or with a Varian "Superscan" double beam spectrophotometer at 412 nM. No difference in kinetic constants were seen when proper corrections were made to account for the bichromatic nature of the ABA-100. In all cases, the observed values of enzyme hydrolysis were corrected to account for spontaneous hydrolysis.

TABLE I

| Substrate | Thrombin | | Trypsin | |
| --- | --- | --- | --- | --- |
| | Kcat | Km | Kcat | Km |
| α-N-toluenesulfonyl arginine | $sec^{-1}$ | $\times 10^5 M$ | $sec^{-1}$ | $\times 10^5 M$ |
| thioethylester | 30.1 | 2.4 | 127 | 1.9 |
| thiobenzylester | 133 | 10 | 161 | 1.8 |
| thioisopropyl ester | 34.1 | 2.2 | 119 | 1.9 |
| thioisobutyl ester | 26.4 | 2.8 | 136 | 1.7 |
| thio-p-chloro-benzylester | 4.8 | 10 | 132 | 1.2 |

Therefore, the compounds of the present invention are useful, for example, in measuring the amount of thrombin released from prothrombin in human plasma. In particular, compounds of the present invention are useful for measuring levels of antithrombin III in plasma samples. Thus, the reagent is added to plasma samples after inhibition by antithrombin III. The hydrolysis product $-S-R_2$ is trapped by 5,5' dithiobis-(2-nitrobenzoic acid) to form a colored product detectable at about 412 nm.

The following examples are intended to illustrate the present invention and not to limit it in scope or spirit.

EXAMPLE I

To 7.0g of α-N-toluenesulfonyl-L-arginine 0.3H₂O (Vega-Fox biochemicals) is added 45 ml of thionyl chloride and the resulting mixture stirred vigorously in a water bath at 15°-20° C. After 6-8 minutes a heavy oil separates and stirring is continued for an additional 8-10 minutes at −15° C. (ice methanol bath). The cooled mixture is treated with 150ml of ethyl ether to form a gummy precipitate. The supernatant liquid is decanted and the residue triturated several times with ether. Upon scratching in chilled ether the gummy material is transformed into a pale yellow solid which is separated from the ether by inverse filtration. Twenty ml of ethyl mercaptan is added to the solid acid chloride and the mixture cooled to 15° C. Twenty-three ml of dimethyl formamide is added with vigorous stirring. After stirring for 30-45 minutes at room temperature, ether is added causing a gum to separate. The gum is dissolved in methylene chloride and reprecipitated with ethyl ether. The product is chromatographed on silica gel eluting with 3–4% water in acetonitrile to provide α-N-(p-toluenesulfonyl)-L-arginine thioethylester hydrochloride having the formula

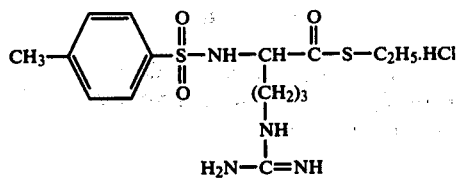

Freeze drying an aqueous solution of the thioester provides a white powder characterized as follows: Rf 0.40 on TLC (10% water in acetonitrile). $[\alpha]_d^{25} = -44°$; analytical data for $C_{15}H_{25}N_4O_3S_2Cl \cdot \frac{1}{2}H_2O$.

Calc. C, 43.10; H, 6.03; N, 13.4; Cl 8.48. Found C, 43.01; H, 6.09; N, 13.36; Cl 8.62.

EXAMPLE II

Following the procedure in Example 1 replacing ethylmercaptan with phenylmethylmercaptan provides α-N-(p-toluenesulfonyl)-L-arginine thiobenzylester hydrochloride. Rf 0.38 in 10% acetonitrile in water.

EXAMPLE III

Following the procedure in Example 1 replacing mercaptan with isobutylmercaptan provides α-N-(p-toluenesulfonyl)-L-arginine thioisobutylester hydrochloride, m.p. 66°–70°, Rf 0.35 acetonitrile—water, 9:1, $[\alpha]_d^{25} - 29$ water.

EXAMPLE IV

Following the procedure in Example 1 replacing ethylmercaptan with isopropylmercaptan provides α-N-(p-toluenesulfonyl)-L-arginine thioisopropylester hydrochloride, Rf 0.33 acetonitrile—water, $[\alpha]_d^{25} - 26$ water.

EXAMPLE V

Following the procedure in Example 1 replacing ethylmercaptan with p-chlorophenylmethyl mercaptan provides α-N-(p-toluenesulfonyl)-L-arginine thio-p-chlorobenzylester.

EXAMPLE VI

Following the procedure in Example 1 replacing α-N-toluenesulfonyl-L-arginine w-th α-N-carbobenzoxy-L-arginine, U.S. Pat. No. 3,884,869, thioethylester hydrochloride of the formula

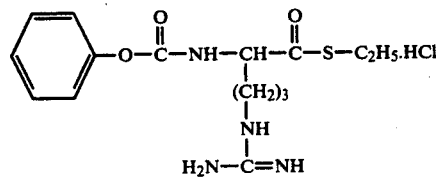

Replacing ethylmercaptan with phenylmethylmercaptan provides α-N-carbobenzoxy-L-arginine thiobenzylester hydrochloride.

EXAMPLE VII

Following the procedure in Example 1 using α-N-benzoylarginine, Archives of Biochemistry and Biophysics 108, 266 (1964) provides α-N-benzoyl-L-arginine-thioethylester hydrochloride having the formula

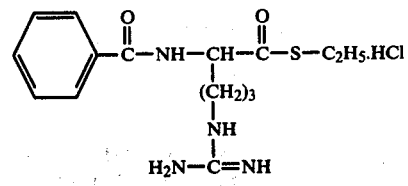

and the free base. Replacing ethylmercaptan with phenylmethylmercaptan provides α-N-benzoyl-L-arginine thiobenzylester hydrochloride.

EXAMPLE VIII

α-N-acetyl arginine prepared by reaction of acetic anhydride with the nitric acid salt of arginine is used to replace α-N-toluenesulfonyl-L-arginine in Example 1 to provide α-N-acetyl-L-arginine thioethylester hydrochloride, having the formula

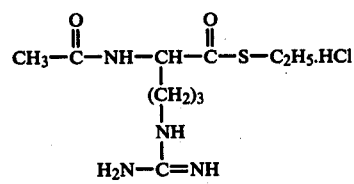

EXAMPLE IX

Following the procedure of Example 1 using α-N-toluenesulfonyllsysine, J. Chem. Soc. 4830, (1957) provides α-N-toluenesulfonyl-L-lysine thioethylester hydrochloride having the formula

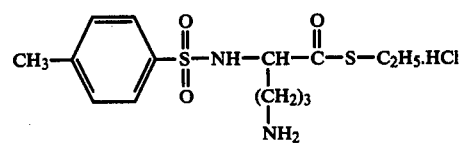

EXAMPLE X

Following the procedure in Example 1 using α-N-toluenesulfonylhomoarginine, J. Prakt. Chem. 312, 1161 (1970) provides α-N-toluenesulfonyl-L-homoarginine thioethylester having the formula

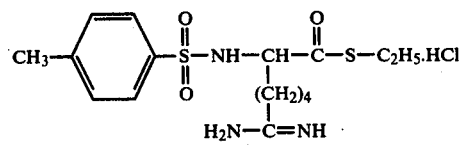

What is claimed is:

1. The biologically compatible acid addition salts of a compound of the formula

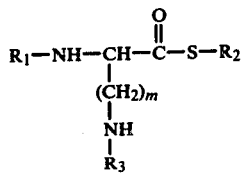

wherein: $R_1$ represents phenylsulfonyl, benzoyl, carbobenzoxy, and the halo, loweralkyl having 1–4 carbon atoms, loweralkoxy having 1–3 carbon atoms, phenyl, or hydroxy substituted derivatives thereof; or alkanoyl having 2–12 carbon atoms; $R_2$ represents alkyl having 1–10 carbon atoms or alkoxyalkyl having 2–6 carbon atoms, cycloalkyl having 5–7 carbon atoms, or benzyl and the halo, lowerlakyl having 1–4 carbon atoms, loweralkoxy having 1–3 carbon atoms, carboxy, hydroxy or phenyl substituted derivatives thereof; $R_3$ represents hydrogen or guanyl; and m is 3 or 4.

2. The biologically compatible acid addition salts of a compound according to claim 1 of the formula

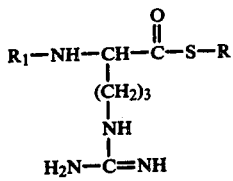

wherein R represents alkyl having 1–6 carbon atoms.

3. The biologically compatible acid addition salts of a compound according to claim 1, of the formula

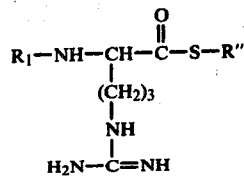

wherein R″ represents benzyl or halobenzyl.

4. The biologically compatible acid addition salts of a compound of the formula

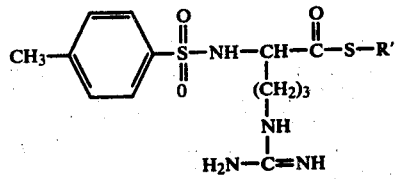

wherein R′ represents alkyl having 1–6 carbon atoms, benzyl or halobenzyl.

5. A compound, according to claim 4 which is α-N-toluenesulfonyl arginine thioethylester hydrochloride.

6. A compound, according to claim 4 which is α-N-toluenesulfonyl arginine thioisopropylester hydrochloride.

7. A compound, according to claim 4 which is α-N-toluenesulfonyl arginine thioisobutylester hydrochloride.

8. A compound, according to claim 3 which is α-N-toluenesulfonyl arginine thiobenzylester hydrochloride.

9. A compound, according to claim 3 which is toluenesulfonyl arginine thio(p-chlorobenzyl) ester hydrochloride.

* * * * *